(12) United States Patent  
Hoffmann-Emery et al.

(10) Patent No.: US 7,579,464 B2
(45) Date of Patent: Aug. 25, 2009

(54) PROCESS FOR PREPARATION OF ENANTIOMERICALLY PURE COMPOUNDS

(75) Inventors: Fabienne Hoffmann-Emery, Weil am Rhein (DE); Roland Jakob-Roetne, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/110,372

(22) Filed: Apr. 28, 2008

(65) Prior Publication Data

US 2008/0293933 A1 Nov. 27, 2008

(30) Foreign Application Priority Data

May 25, 2007 (EP) .................................. 07108904

(51) Int. Cl.
*C07D 223/18* (2006.01)
(52) U.S. Cl. ..................................................... 540/522
(58) Field of Classification Search .................. 540/522
See application file for complete search history.

(56) References Cited

U.S. PATENT DOCUMENTS 6,528,505 B1 3/2003 Audia et al.
2005/0075327 A1 4/2005 Flohr et al.

FOREIGN PATENT DOCUMENTS

WO WO 2005/023749 3/2005
WO WO 2005/023772 3/2005

OTHER PUBLICATIONS

Wiesner et al., J. Am. Chem. Soc. 1955, vol. 77 pp. 675-683.
Yang, M. et al, *Bioorganic & Medicinal Chem. Letters*, 17:14(2007) 3910-3915.

*Primary Examiner*—Bruck Kifle
(74) *Attorney, Agent, or Firm*—George W. Johnston; Patricia S. Rocha-Tramaloni; Gene J. Yao

(57) ABSTRACT

The invention relates to a process for the optical resolution of a dibenzo[b,d]azepinone derivative of formula II,

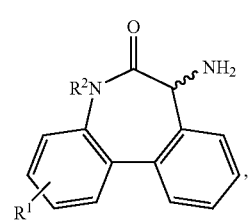

wherein $R^1$ is hydrogen or halogen and $R^2$ is either $C_{1-4}$-alkyl optionally substituted with $C_{3-7}$-cycloalkyl or benzyl which is optionally substituted with $C_{1-4}$-alkoxy, to obtain a (S)-7-amino-5H,7H-dibenzo[b,d]azepin-6-one of formula I,

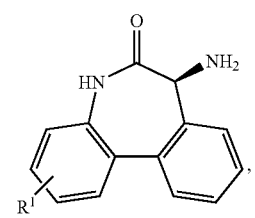

wherein $R^1$ is as in the compound of formula II. The (S)-7-amino-5H,7H-dibenzo[b,d]azepin-6-one of formula I can be used as a chiral building block for the preparation of malonamide derivatives which have the potential to act as γ-secretase inhibitors and therefore may be useful in the treatment of Alzheimer's disease and cancer.

13 Claims, No Drawings

PROCESS FOR PREPARATION OF ENANTIOMERICALLY PURE COMPOUNDS

PRIORITY TO RELATED APPLICATION(S)

This application claims the benefit of European Patent Application No. 07108904.9, filed May 25, 2007, which is hereby incorporated by reference in its entirety.

BACKGROUND OF THE INVENTION

The invention relates to a novel process for the preparation of an enantiomerically pure 7-amino-5H,7H-dibenzo[b,d]azepin-6-one. The (S)-7-amino-5H,7H-dibenzo[b,d]azepin-6-one enantiomer can be used as a chiral building block for the preparation of malonamide derivatives which have the potential to act as γ-secretase inhibitors and therefore may be useful in the treatment of Alzheimer's disease and cancer.

The preparation of enantiomerically pure 7-amino-5H,7H-dibenzo[b,d]azepin-6-one has been accomplished using HPLC over a chiral stationary phase. However, such methods are suitable at laboratory scale only. The object of the present invention, therefore, is the production of chiral 7-amino-5H, 7H-dibenzo[b,d]azepin-6-one with high enantiomeric excess and with a process which is applicable on a technical scale.

SUMMARY OF THE INVENTION

The present invention relates to a process for the preparation of an enantiomerically pure 7-amino-5H,7H-dibenzo[b,d]azepin-6-one of the formula Ia,

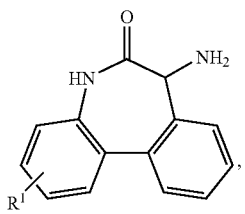

Ia wherein $R^1$ is hydrogen or halogen, comprising the optical resolution of a dibenzo[b,d]azepinone derivative of the formula II,

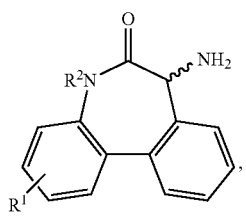

II wherein $R^1$ is as in the compound of formula Ia and $R^2$ is either $C_{1-4}$-alkyl optionally substituted with cycloalkyl or benzyl which is optionally substituted with $C_{1-4}$-alkoxy, using a chiral menthyl chloroformate.

Another aspect of the present invention is a compound of the formula IIIa,

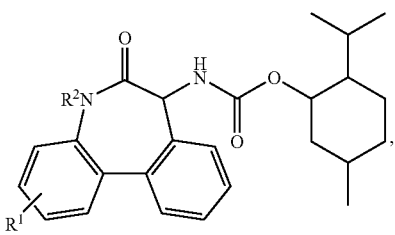

IIIa wherein $R^1$ is hydrogen or halogen and $R^2$ is either $C_{1-4}$-alkyl optionally substituted with cycloalkyl or benzyl which is optionally substituted with $C_{1-4}$-alkoxy; or an optical isomer thereof.

Yet another aspect of the present invention is a process for the preparation of a malonamide derivative of formula IV,

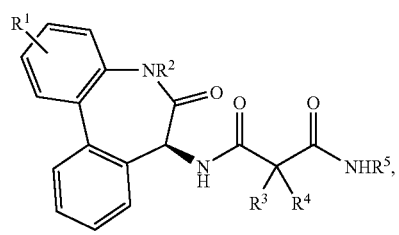

IV wherein:

$R^1$ is hydrogen or halogen;

$R^2$ is either $C_{1-4}$-alkyl optionally substituted with cycloalkyl or benzyl which is optionally substituted with $C_{1-4}$-alkoxy;

$R^3$ and $R^4$ are each independently selected from the group consisting of: hydrogen, lower alkyl, lower alkoxy, phenyl and halogen;

$R^5$ is selected from the group consisting of: lower alkyl, lower alkynyl, —$(CH_2)_n$—O-lower alkyl, —$(CH_2)_n$—S-lower alkyl, —$(CH_2)_n$—CN, —$(CR'R'')_n$—$CF_3$, —$(CR'R'')_n$—$CHF_2$, —$(CR'R'')_n$—$CH_2F$, —$(CH_2)_n$—C(O)O-lower alkyl, —$(CH_2)_n$-halogen, and —$(CH_2)_n$-cycloalkyl optionally substituted by one or more substituents selected from the group consisting of phenyl, halogen and —$CF_3$;

R' and R'' are each independently selected from the group consisting of: hydrogen, lower alkyl, lower alkoxy, halogen and hydroxy; and n is 0, 1, 2, 3, or 4.

Such a process comprises the preparation of an enantiomerically pure (S)-7-amino-5H,7H-dibenzo[b,d]azepin-6-one using the process described above.

DETAILED DESCRIPTION OF THE INVENTION

The invention relates to a novel process for the preparation of an enantiomerically pure 7-amino-5H,7H-dibenzo[b,d]azepin-6-one of the formula Ia,

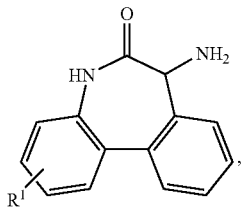

Ia wherein R¹ is hydrogen or halogen. In particular, the present invention relates to the preparation of (S)-7-amino-5H,7H-dibenzo[b,d]azepin-6-one of the formula I,

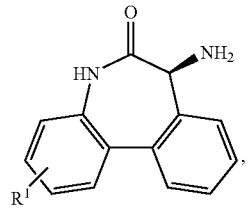

I wherein R¹ is hydrogen or halogen.

(S)-7-amino-5H,7H-dibenzo[b,d]azepin-6-one is a chiral building block for the synthesis of malonamide derivatives which have the potential to act as γ-secretase inhibitors and therefore may be useful in the treatment of Alzheimer's disease and cancer. Such malonamide compounds are disclosed, for example, in PCT Publication WO 2005/023772.

The process of the present invention is particularly useful in the synthesis of malonamide compounds of the formula IV,

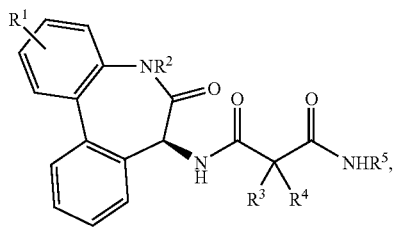

IV wherein R¹ is hydrogen or halogen and R² is either $C_{1-4}$-alkyl optionally substituted with cycloalkyl or benzyl which is optionally substituted with $C_{1-4}$-alkoxy;

R³ and R⁴ are each independently selected from the group consisting of: hydrogen, lower alkyl, lower alkoxy, phenyl and halogen;

R⁵ is selected from the group consisting of: lower alkyl, lower alkynyl, —(CH₂)$_n$—O-lower alkyl, —(CH₂)$_n$—S-lower alkyl, —(CH₂)$_n$—CN, —(CR'R")$_n$—CF₃, —(CR'R")$_n$—CHF₂, —(CR'R")$_n$—CH₂F, —(CH₂)$_n$—C(O)O-lower alkyl, —(CH₂)$_n$-halogen, and —(CH₂)$_n$-cycloalkyl optionally substituted by one or more substituents selected from the group consisting of phenyl, halogen and —CF₃;

R' and R" are each independently selected from the group consisting of: hydrogen, lower alkyl, lower alkoxy, halogen and hydroxy; and n is 0, 1, 2, 3, or 4;

and their pharmaceutically suitable acid addition salts and optically pure enantiomers, and racemic or diasteromeric mixtures of stereoisomers of such compounds.

As used herein, the term "lower alkyl" denotes a saturated straight- or branched-chain alkyl group containing from 1 to 7 carbon atoms, for example, menthyl, ethyl, propyl, isopropyl, n-butyl, i-butyl, 2-butyl, t-butyl and the like. Preferred lower alkyl groups are groups with 1-4 carbon atoms, referred to herein as "$C_{1-4}$-alkyl" groups.

As used herein, the term "lower alkynyl" denotes an unsaturated straight- or branched-carbon chain containing from 2 to 7 carbon atoms and containing at least one triple bond.

The term "cycloalkyl" denotes a saturated carbocyclic group containing 3 to 7 carbon atoms. Examples thereof include cyclopropyl, cyclobutyl, cyclopentyl, and cyclohexyl. A preferred cycloalkyl is cyclopropyl.

The term "halogen" denotes chlorine, iodine, fluorine or bromine.

The term "lower alkoxy" denotes a group wherein an alkyl residue, as defined above, is attached via an oxygen atom to the remainder of the molecule. As used herein, the term "$C_{1-4}$-alkoxy" refers to a lower alkoxy group wherein the alkyl residue is a $C_{1-4}$-alkyl.

The expression "—(CR'R")$_n$—" may be, for example —CH₂—, —CH₂—CH₂—, —CH₂—CH₂—CH₂—, —CH₂—CF₂—, —CH₂—CH₂—CF₂—, —CH₂—CH₂—CH(OCH₃)—, —CH₂CH(OH)— or —C(CH₃)₂—CH(OH)—.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane sulfonic acid, p-toluene sulfonic acid and the like.

The preparation of enantiomerically pure 7-amino-5H,7H-dibenzo[b,d]azepin-6-one of formula I,

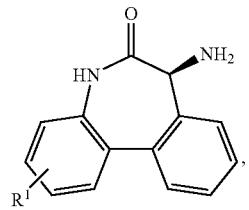

I wherein R¹ is hydrogen or halogen, has been accomplished by HPLC over a chiral stationary phase (see PCT Publication WO 2005/023772). However, such methods are suitable at laboratory scale only. The object of the present invention, therefore, is the production of chiral 7-amino-5H,7H-dibenzo[b,d]azepin-6-one with high enantiomeric excess and with a process which is applicable on a technical scale.

The present invention relates to a process for the preparation of an enantiomerically pure 7-amino-5H,7H-dibenzo[b,d]azepin-6-one comprising the optical resolution of a dibenzo[b,d]azepinone derivative of formula II,

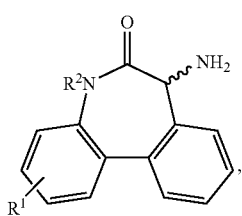

using a chiral menthyl chloroformate, wherein $R^1$ is hydrogen or halogen and $R^2$ is either $C_{1-4}$-alkyl optionally substituted with cycloalkyl or benzyl which is optionally substituted with $C_{1-4}$-alkoxy. In a preferred embodiment, $R^1$ is hydrogen or fluorine and $R^2$ is $C_{1-4}$-alkoxy benzyl. In a particularly preferred embodiment, $R^1$ is hydrogen and $R^2$ is 4-methoxy-benzyl.

The dibenzo[b,d]azepinone derivatives of formula II can be manufactured, for example, as outlined in the scheme below exemplified for the compounds wherein $R^1$ is hydrogen and $R^2$ is 4-methoxy-benzyl.

The synthesis of 3 can, for example, be performed according to J. Am. Chem. Soc., 1955, 77, 675 by the 2-step route described in the scheme above. In a first step the N-chloroacetamide 2 is formed from 1 and subsequently ring closure to 3 is effected by refluxing 2 in 1,3-dichlorobenzene in the presence of aluminum chloride.

Introduction of the amino group and the formation of 6 can be accomplished by protecting the lactam function of 3 thereby forming 4, then by converting 4 into the oxime 5 and then by reducing 5 to the racemic amine 6 as described in U.S. Pat. No. 6,528,505.

The suitable menthyl chloroformate is either the (−)-menthyl chloroformate or the (+)-menthyl chloroformate, preferably the (−)-menthyl chloroformate.

In a preferred process, (−)-menthyl chloroformate is used and (S)-7-amino-5H,7H-dibenzo[b,d]azepin-6-one is produced.

The optical resolution usually comprises the following steps:

a) reacting the aforementioned compound of formula II with (−)-menthyl chloroformate to produce the compound of formula III,

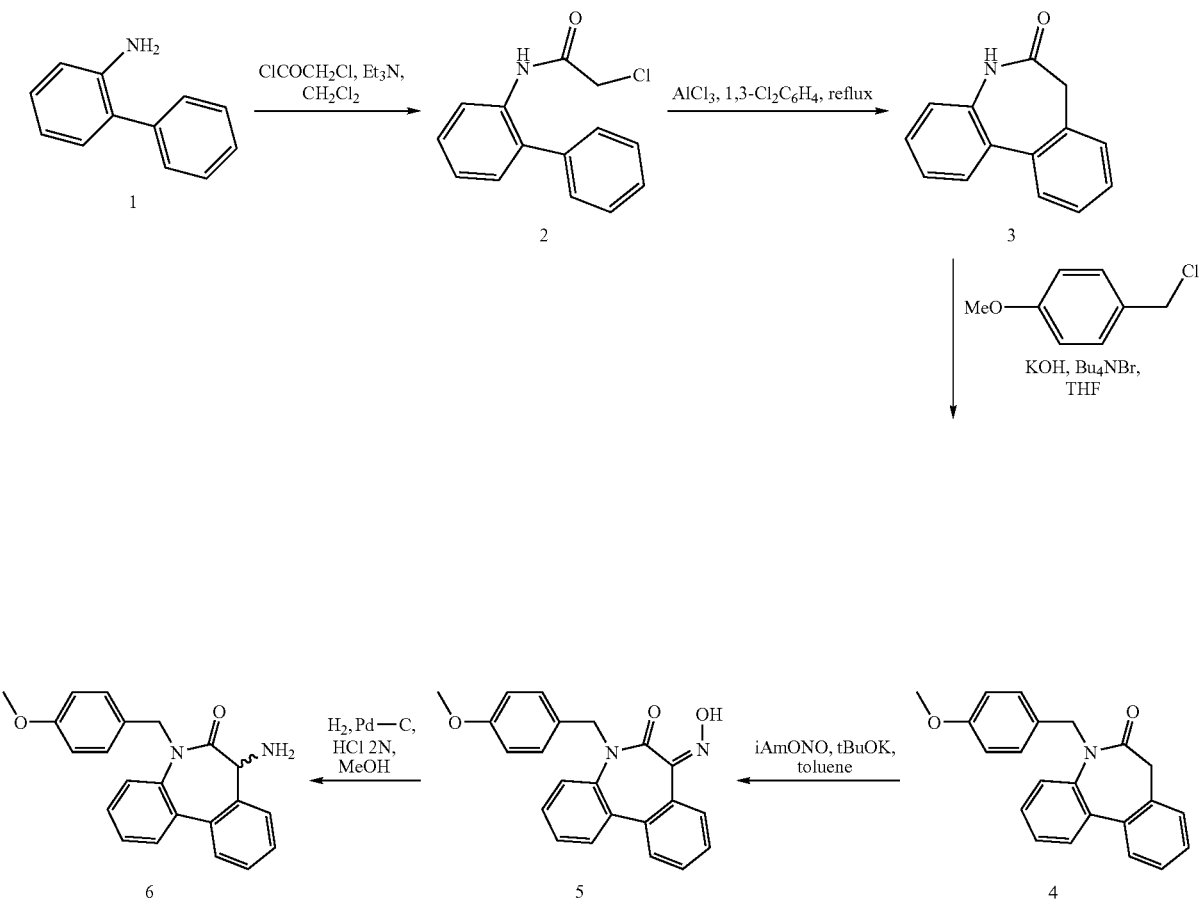

Scheme 1

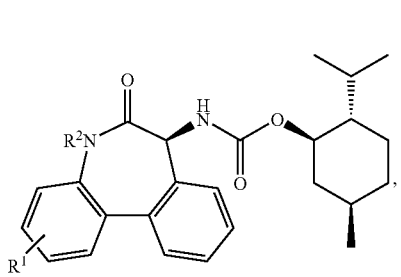

wherein $R^1$ and $R^2$ are as in the compound of formula II, and b) cleaving the carbamate function of said compound of formula III and the protecting group $R^2$ in the presence of an acid to produce 7-amino-5H,7H-dibenzo[b,d]azepin-6-one.

In a preferred embodiment of the present invention $R^1$ is hydrogen or fluorine and $R^2$ is a $C_{1-4}$-alkoxy benzyl. In a particularly preferred embodiment, $R^1$ is hydrogen and $R^2$ is 4-methoxy-benzyl.

The formation of the epimer of the menthyl carbamate of formula III in step a) is usually performed in the presence of an inorganic or organic base in an organic solvent.

Suitable inorganic bases can be selected from alkali carbonates and alkali bicarbonates. Preferably sodium carbonate is used.

Suitable organic bases include trialkyl amine and pyridine. Preferably, pyridine is used.

Suitable organic solvents include cyclic ethers such as tetrahydrofuran, halogenated solvents such as methylene chloride, N-methylpyrrolidone, and N,N'-dimethylformamide.

The conversion is performed at a temperature from 0° C. to 100° C. and preferably at room temperature.

Recovery of the preferred epimer of the menthyl carbamate of formula III can be recovered by selective crystallization with a suitable solvent.

Suitable solvents for the selective crystallization are heptane, ethylacetate, diisopropylether, toluene, and tert-butylmethylether, with heptane and ethylacetate being preferred.

The desired epimer can be obtained with a diastereomeric excess of $\geq 99\%$.

The undesired epimer of the menthyl carbamate remains in the mother liquor. A partial isomerization to the desired epimer of the menthyl carbamate of formula III can be achieved by a treatment of the material recovered from the mother liquor with lithium diisopropyl amide at about −75° C. in a suitable organic solvent, such as tetrahydrofuran, and subsequently with chlorotrimethylsilane at −75° C. to 50° C. The desired isomer can finally be recovered, after hydrolysis at room temperature to 50° C., by extraction e.g. with ethyl acetate from the reaction mixture.

A further embodiment of the present invention is the menthylcarbamate of formula IIIa,

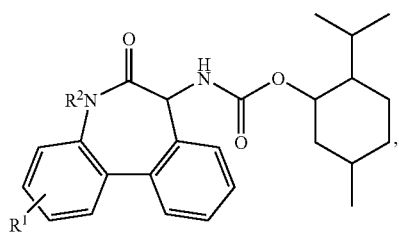

wherein $R^1$ is hydrogen or halogen and $R^2$ is either $C_{1-4}$-alkyl optionally substituted with cycloalkyl or benzyl which is optionally substituted with $C_{1-4}$-alkoxy; or an optical isomer thereof. A preferred embodiment of the present invention is the epimer of the menthyl carbamate of formula III,

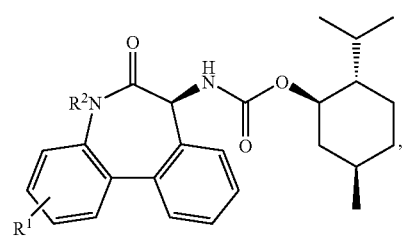

wherein $R^1$ is hydrogen or halogen and $R^2$ is either $C_{1-4}$-alkyl optionally substituted with cycloalkyl or benzyl which is optionally substituted with $C_{1-4}$-alkoxy.

In a preferred embodiment, $R^1$ is hydrogen or fluorine and $R^2$ is $C_{1-4}$-alkoxy benzyl. In a particularly preferred embodiment, $R^1$ is hydrogen and $R^2$ is 4-methoxy-benzyl.

The cleavage of the carbamate function of the compound of formula III and the cleavage of the protecting group $R^2$ in step b) is performed in the presence of an acid.

Suitable acids include trifluoro acetic acid, trifluoromethanesulfonic acid, methanesulfonic acid, sulfuric acid, and mixtures thereof. Preferably, trifluoro acetic acid and trifluoromethanesulfonic acid are used.

The reaction is usually performed in the presence of an organic solvent which can be selected from the group consisting of methylenechloride, tetrahydrofuran, tert-butylmethylether and N-methylpyrrolidone.

Recovery of the desired (S)-7-amino-5H,7H-dibenzo[b,d]azepin-6-one of formula I can happen according to methods known to the skilled in the art.

The process described above is particularly useful in the synthesis of malonamide compounds of formula IV,

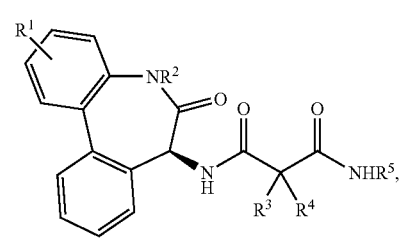

wherein:

R¹ is hydrogen or halogen;

R² is either $C_{1-4}$-alkyl optionally substituted with cycloalkyl or benzyl which is optionally substituted with $C_{1-4}$-alkoxy;

R³ and R⁴ are each independently selected from the group consisting of: hydrogen, lower alkyl, lower alkoxy, phenyl and halogen;

R⁵ is selected from the group consisting of: lower alkyl, lower alkynyl, —(CH₂)$_n$—O-lower alkyl, —(CH₂)$_n$—S-lower alkyl, —(CH₂)$_n$—CN, —(CR'R")$_n$—CF₃, —(CR'R")$_n$—CHF₂, —(CR'R")$_n$—CH₂F, —(CH₂)$_n$—C(O)O-lower alkyl, —(CH₂)$_n$-halogen, and —(CH₂)$_n$-cycloalkyl, wherein said R⁵ is optionally substituted by one or more substituents selected from the group consisting of phenyl, halogen and —CF₃;

R' and R" are each independently selected from the group consisting of: hydrogen, lower alkyl, lower alkoxy, halogen and hydroxy; and n is 0, 1, 2, 3, or 4.

The conversion of the (S)-7-amino-5H,7H-dibenzo[b,d]azepin-6-one to the malonamide derivatives of formula IV is disclosed in the PCT Publication WO 2005/023772.

The following examples shall illustrate the invention without limiting it.

EXAMPLE 1

7-amino-5-(4-methoxy-benzyl)-5H,7H-dibenzo[b,d]azepin-6-one

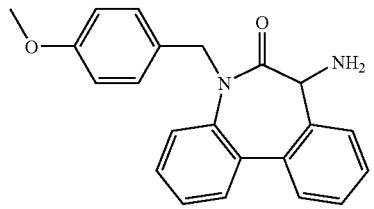

a) N-biphenyl-2-yl-2-chloro-acetamide

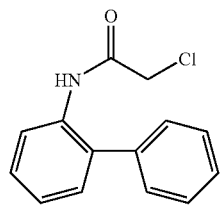

Triethylamine (26.7 g) was added to a solution of 2-aminobiphenyl (41.4 g) in dichloromethane (248 mL) at room temperature. The solution obtained was cooled to −18° C. and chloracetylchloride (28.8 g) was slowly added. The suspension obtained was further stirred for 1 hour at 0° C. and for 15 hours at room temperature. Dichloromethane (150 mL), ice-water (500 mL), water (500 mL) and saturated aqueous NaHCO₃ (150 mL) were added. After stirring, the phases were separated, the organic phase was washed with half-saturated aqueous NaCl (1000 mL) and the aqueous phases were extracted with dichloromethane (250 mL). The combined organic layers were dried (MgSO₄) and concentrated under vacuum to a weight of ca. 100 g. After 40 minutes stirring at room temperature, the precipitate was filtered off, washed with dichloromethane (80 mL) and dried under high vacuum to afford N-biphenyl-2-yl-2-chloro-acetamide (8.6 g, 14.5%) as white crystals. The filtrate was further concentrated under reduced pressure to a weight of ca. 115 g and hexane (100 mL) was added dropwise. After 1 hour of stirring at room temperature, the precipitate was filtered off, washed with 3 portions of hexane/dichloromethane 4:1 (22 mL) and dried under high vacuum affording N-biphenyl-2-yl-2-chloro-acetamide (31.2 g, 53.0%) as a grey powder. The filtrate was concentrated under reduced pressure to a weight of ca. 90 g and stirred for 1 hour at room temperature. The precipitate was filtered off, washed with 2 portions of hexane/dichloromethane 4:1 (17 mL) and dried under high vacuum affording N-biphenyl-2-yl-2-chloro-acetamide (10.8 g, 18.3%) as a grey powder.

MS(ISP): m/e=508 (2M+NH₄⁺, 25), 262 (M+NH₄⁺, 78) 246 (M+H⁺, 100).

b) 5H,7H-dibenzo[b,d]azepin-6-one

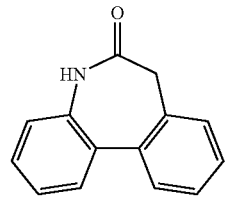

AlCl₃ (12.1 g) was added to a solution of N-biphenyl-2-yl-2-chloro-acetamide (9.9 g) in 1,3-dichlorobenzene (99 mL). The reaction mixture was stirred for 24 hours at 170° C., cooled to 0° C. and poured into ice-water (1500 mL). The suspension obtained was filtered off, the precipitate washed with water (250 mL), 2 portions of hexane/dichloromethane 4:1 (25 mL), 2 portions of water (125 mL) and 2 portions of hexane (25 mL) affording 5H,7H-dibenzo[b,d]azepin-6-one (6.9 g, 82.5%) as an off-white powder.

MS(ISP): m/e=232 (M+Na⁺, 14), 210 (M+H⁺, 100).

c) 5-(4-methoxy-benzyl)-5H,7H-dibenzo[b,d]azepin-6-one

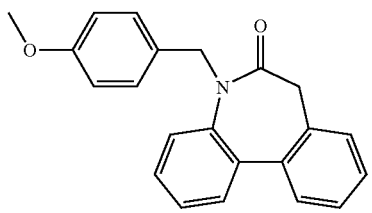

Tetrabutylammonium bromide (0.82 g), potassium hydroxide (1.7 g) and p-methoxybenzylchloride (4.3 g), in that order, were added to a suspension of 5H,7H-dibenzo[b,d]azepin-6-one (5.63 g) in THF (112.5 mL). The reaction mixture was stirred 3 hours at room temperature. Dichloromethane (250 mL) and half-saturated aqueous NaCl (1500 mL) were added. The phases were separated, the organic phase was washed with half-saturated aqueous NaCl (1000 mL) and the aqueous layers were extracted with dichloromethane (150 mL) three times. The combined organic layers were dried (MgSO$_4$), concentrated under reduced pressure and dried under high vacuum affording 5-(4-methoxy-benzyl)-5H,7H-dibenzo[b,d]azepin-6-one (9.5 g, quant.) as a brown oil, which was used in the next step without further purification.

MS(ISP): m/e=659 (2M+H$^+$, 60), 352 (M+Na$^+$, 14), 330 (M+H$^+$, 100), 242 (52), 222 (87).

d) 5-(4-methoxy-benzyl)-5H-dibenzo[b,d]azepine-6,7-dione 7-oxime

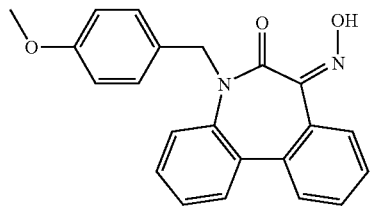

Potassium tert-butylate (7.6 g) was added slowly to a solution of 5-(4-methoxy-benzyl)-5H,7H-dibenzo[b,d]azepin-6-one (14.6 g) in THF (146 mL) cooled to 0° C. After 10 minutes of stirring at 0° C., isopentylnitrite (10.6 g) was slowly added and the reaction mixture was further stirred for 105 minutes at 0° C. The reaction mixture was poured onto half-saturated aqueous NaCl (1200 mL), cooled to 0° C. and dichloromethane (500 mL) was added. The phases were separated, the organic phase was washed with half-saturated aqueous NaCl (1200 mL) and the aqueous layers were extracted with dichloromethane (250 mL) twice. The combined organic layers were dried (MgSO$_4$), concentrated under reduced pressure and dried under high vacuum affording 5-(4-methoxy-benzyl)-5H-dibenzo[b,d]azepine-6,7-dione 7-oxime (18.4 g, quant.) as a yellow foam, which was used in the next step without further purification.

MS(ISP): m/e=739 (2M+Na$^+$, 20), 717 (2M+H$^+$, 79), 381 (M+Na$^+$, 47), 359 (M+H$^+$, 100), 251 (28).

e) 7-amino-5-(4-methoxy-benzyl)-5H,7H-dibenzo[b,d]azepin-6-one hydrochloride

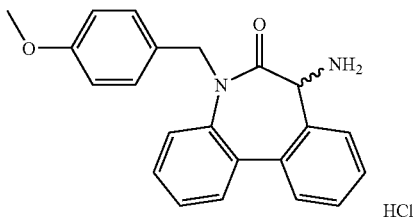

Aqueous HCl 2N (20.8 mL) was added to a solution of 5-(4-methoxy-benzyl)-5H-dibenzo[b,d]azepine-6,7-dione 7-oxime (8.3 g) in methanol (83.0 mL). Pd/C (10% weight, 540 mg) was added to the reaction mixture and the system was stirred under 10 bar H$_2$ at 50° C. for 2 days. After exchanging H$_2$ for Ar, the reaction mixture was filtered, concentrated under reduced pressure and dried under high vacuum yielding 7-amino-5-(4-methoxy-benzyl)-5H,7H-dibenzo[b,d]azepin-6-one hydrochloride (8.7 g, quant.) as a light yellow powder. This powder was suspended in acetonitrile (43 mL) and stirred 2 hours at room temperature. The precipitate was filtered off, washed with acetonitrile and dried under reduced pressure yielding 7-amino-5-(4-methoxy-benzyl)-5H,7H-dibenzo[b,d]azepin-6-one hydrochloride (8.3 g, 96%) as an off-white powder.

MS(ISP): m/e=367 (M+Na$^+$, 13), 345 (M+H$^+$, 100).

f) 7-amino-5-(4-methoxy-benzyl)-5H,7H-dibenzo[b,d]azepin-6-one

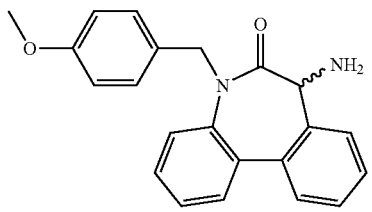

Aqueous HCl 3N (18.0 mL) was added to a solution of 5-(4-methoxy-benzyl)-5H-dibenzo[b,d]azepine-6,7-dione 7-oxime (10.9 g.) in methanol (150.0 mL). Pd/C (10% weight, 1.08 g) was added to the reaction mixture and the system was stirred under 10 bar H$_2$ at 50° C. for 18 hours. After exchanging H$_2$ for Ar, the reaction mixture was filtered, water (150 mL) was added and methanol was removed under reduced pressure. The aqueous phase was extracted with EtOAc (50.0 mL), the organic phase was washed with water (50.0 mL) and the aqueous phases were extracted separately with the same portion of EtOAc (30.0 mL). Dichloromethane (100.0 mL) was added to the combined aqueous phases and aqueous NaOH 0.9 M (65.5 mL) was added slowly to bring the aqueous phase to pH=ca. 7. After 10 minutes of stirring, the phases were separated; the aqueous phase was extracted with dichloromethane (50.0 mL). The combined organic phases were dried (MgSO$_4$) and concentrated under reduced pressure yielding 7-amino-5-(4-methoxy-benzyl)-5H,7H-dibenzo[b,d]azepin-6-one (9.7 g, 91%) as yellow oil.

MS(ISP): m/e=367 (M+Na$^+$, 50), 345 (M+H$^+$, 100), 208 (34).

EXAMPLE 2

(S)-7-amino-5H,7H-dibenzo[b,d]azepin-6-one

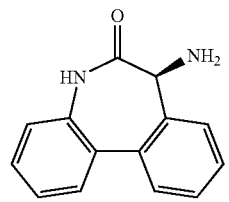

a) [(S)-5-(4-methoxy-benzyl)-6-oxo-6,7-dihydro-5H-dibenzo[b,d]azepin-7-yl]-carbamic Acid (1R,2S,5R)-2-isopropyl-5-methyl-cyclohexyl Ester

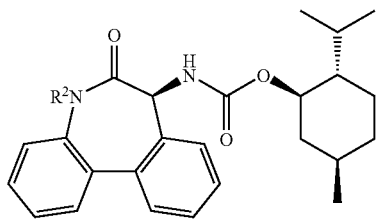

Water (40 mL) was added to a yellow solution of 7-amino-5-(4-methoxy-benzyl)-5H,7H-dibenzo[b,d]azepin-6-one (7.45 g) in THF (40 mL) at room temperature forming a light yellow suspension. To this suspension were added $K_2CO_3$ (5.53 g) in one portion and, after 15 minutes of stirring, (−)-(1R)-menthyl chloroformate (4.96 g) was added within 30 minutes. The dropping funnel was washed with THF. The emulsion was stirred for 105 minutes at room temperature. Heptane (486 mL) was added within 40 minutes and, after 60 more minutes of stirring, the precipitate was filtered off, washed with heptane, water, and then heptane in that order and dried under vacuum at 55° C. to afford [(S)-5-(4-methoxy-benzyl)-6-oxo-6,7-dihydro-5H-dibenzo[b,d]azepin-7-yl]-carbamic acid (1R,2S,5R)-2-isopropyl-5-methyl-cyclohexyl ester (4.75 g, 45%), d.e.=99.8:0.2 (HPLC), as a white powder.

MS(ISP): m/e=549 (M+Na$^+$, 20), 527 (M+H$^+$, 100), 389 (35), 345 (43).

The phases of the filtrate were separated. The organic phase was washed with brine:water 1:1 (400 mL) and the aqueous layers was extracted with heptane (150 mL). The combined organic phases were dried (MgSO$_4$), concentrated under reduced pressure and dried under high vacuum at 50° C. to afford a foam (6.66 g, 63%), d.e.=4.4:95.6 (HPLC).

MS(ISP): m/e=549 (M+Na$^+$, 22), 527 (M+H$^+$, 100), 389 (29), 345 (45).

b) (S)-7-amino-5H,7H-dibenzo[b,d]azepin-6-one

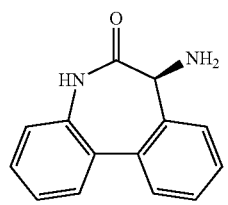

To a solution of [(S)-5-(4-methoxy-benzyl)-6-oxo-6,7-dihydro-5H-dibenzo[b,d]azepin-7-yl]-carbamic acid (1R,2S,5R)-2-isopropyl-5-methyl-cyclohexyl ester (7.79 g) in $CH_2Cl_2$ (195 mL) cooled to 0° C. was added trifluroacetic acid (34.4 g) over 15 minutes followed by trifluoromethansulfonic acid (11.3 g) within 15 minutes. The purple solution obtained was stirred for 16 hours at room temperature and concentrated under reduced pressure at 40° C. according a dark red oil, which was partitioned between $CH_2Cl_2$ and half-saturated aqueous NaHCO$_3$. The phases were separated and the aqueous phase was extracted with $CH_2Cl_2$. The combined organic layers were dried (MgSO$_4$) and concentrated under vacuum affording 94.0 g of the yellow solution. The solution was diluted with CH$_3$OH (66 mL) and HCl aqueous 2N was added drop wise at room temperature. After 30 minutes of stirring, the solution was concentrated under reduced pressure. The solid residue was triturated with $CH_2Cl_2$ at room temperature for 16 hours, filtered off, washed with $CH_2Cl_2$ and dried under high vacuum at 75° C. yielding (S)-7-amino-5H,7H-dibenzo[b,d]azepin-6-one (3.64 g, 94%) as a white to light pink powder of mp>225° C.

MS(ISP): m/e=225 (M+H$^+$, 100).

c) Racemization of [(R)-5-(4-methoxy-benzyl)-6-oxo-6,7-dihydro-5H-dibenzo[b,d]azepin-7-yl]-carbamic Acid (1R,2S,5R)-2-isopropyl-5-methyl-cyclohexyl Ester and Isolation of [(S)-5-(4-methoxy-benzyl)-6-oxo-6,7-dihydro-5H-dibenzo[b,d]azepin-7-yl]-carbamic Acid (1R,2S,5R)-2-isopropyl-5-methyl-cyclohexyl Ester To a solution of [(R)-5-(4-methoxy-benzyl)-6-oxo-6,7-dihydro-5H-dibenzo[b,d]azepin-7-yl]-carbamic acid (1R,2S,5R)-2-isopropyl-5-methyl-cyclohexyl ester (5.58 g) in THF (20 mL) cooled to −75° C. was added lithium diisopropylamide (2M solution in THF, 15 mL) within 60 minutes. The reaction mixture was stirred for 5 hours at −75° C., chlorotrimethylsilane (4.6 mL) was added within 35 minutes and the reaction mixture was stirred for 15 hours at room temperature. An ice-water mixture (50 mL) was added and, after 2.5 hours stirring, EtOAc (200 mL) and brine:water 1:1 (400 mL) were added. The phases were separated, the organic phase was washed with brine:water 1:1 (300 mL) twice and the aqueous phases were extracted with EtOAc (100 mL) twice. The combined organic layers were dried (MgSO$_4$) and concentrated under reduced pressure until a weight of 15.8 g was obtained. The suspension obtained was filtered off and the precipitate was dried under vacuum at room temperature affording [(S)-5-(4-methoxy-benzyl)-6-oxo-6,7-dihydro-5H-dibenzo[b,d]azepin-7-yl]-carbamic acid (1R,2S,5R)-2-isopropyl-5-methyl-cyclohexyl ester (1.75 g, 31.5%), with d.e.=99.2:0.8 (HPLC), as a white powder. Heptane (132 mL) was added to the filtrate and, after 2 days at room temperature, the precipitate was filtered off affording a ca. 1:1 mixture of [(R)-5-(4-methoxy-benzyl)-6-oxo-6,7-dihydro-5H-dibenzo[b,d]azepin-7-yl]-carbamic acid (1R,2S,5R)-2-isopropyl-5-methyl-cyclohexyl ester and of [(S)-5-(4-methoxy-benzyl)-6-oxo-6,7-dihydro-5H-dibenzo[b,d]azepin-7-yl]-carbamic acid (1R,2S,5R)-2-isopropyl-5-methyl-cyclohexyl ester. The filtrate was concentrated under reduced pressure and dried under high vacuum affording [(R)-5-(4-methoxy-benzyl)-6-oxo-6,7-dihydro-5H-dibenzo[b,d]azepin-7-yl]-carbamic acid (1R,2S,5R)-2-isopropyl-5-methyl-cyclohexyl ester (3.5 g, 64% HPLC ISTD, 40%), d.e.=96.9:3.1 as a yellow oil.

The invention claimed is:

1. A process for the preparation of an enantiomerically pure 7-amino-5H,7H-dibenzo[b,d]azepin-6-one of the formula Ia,

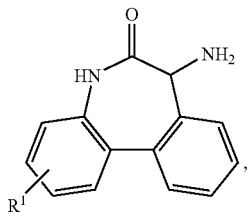

wherein R¹ is hydrogen or halogen, comprising the optical resolution of a dibenzo[b,d]azepinone derivative of the formula II,

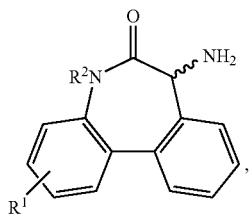

wherein R¹ is as in the compound of formula Ia and R² is either $C_{1-4}$-alkyl optionally substituted with cycloalkyl or benzyl which is optionally substituted with $C_{1-4}$-alkoxy, using a chiral menthyl chloroformate.

2. A process according to claim 1, characterized in that the 7-amino-5H,7H-dibenzo[b,d]azepin-6-one formed is an (S)-7-amino-5H,7H-dibenzo[b,d]azepin-6-one of formula I,

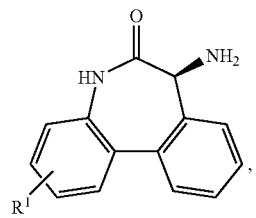

wherein R¹ is as in the compound of formula Ia, and said chiral menthyl chloroformate is (−)-menthyl chloroformate.

3. A process according to claim 1, characterized in that said optical resolution comprises:
a) reacting said compound of formula II with (−)-menthyl chloroformate to produce the compound of formula III,

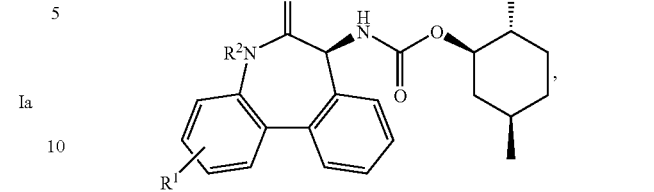

wherein R¹ and R² are as in said compound of formula II, and
b) cleaving the carbamate function of said compound of formula III and the protecting group R² in the presence of an acid to produce said 7-amino-5H,7H-dibenzo[b,d] azepin-6-one.

4. A process according to claim 3, characterized in that, for the formation of said epimer of the menthyl carbamate of formula III in step a), a base is present.

5. A process according to claim 3, characterized in that step a) is performed in an organic solvent.

6. A process according to claim 3, characterized in that, in step a), said compound formula III is recovered by way of a selective crystallization with an organic solvent.

7. A process according to claim 3, characterized in that, for the cleavage of the carbamate function of said compound of formula III and the protecting group R² in step b), trifluoroacetic acid and trifluoromethanesulfonic acid is used.

8. A process according to claim 1, characterized in that R¹ is hydrogen or fluorine and R² is $C_{1-4}$-alkoxy benzyl.

9. A process according to claim 1, characterized in that R¹ is hydrogen and R² is 4-methoxy-benzyl.

10. A compound of formula IIIa,

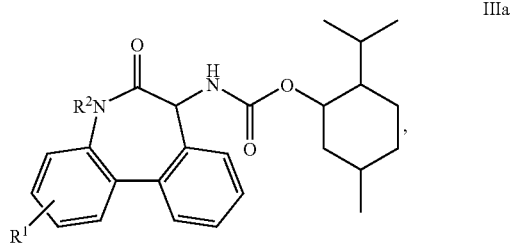

wherein R¹ is hydrogen or halogen and R² is either $C_{1-4}$-alkyl optionally substituted with cycloalkyl or benzyl which is optionally substituted with $C_{1-4}$-alkoxy;
or an optical isomer thereof.

11. A compound of claim 10 wherein said compound is of formula III,

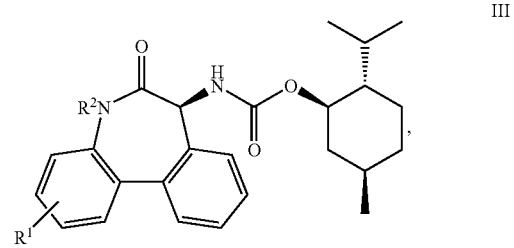

wherein R¹ is hydrogen or halogen and R² is either $C_{1-4}$-alkyl optionally substituted with cycloalkyl or benzyl which is optionally substituted with $C_{1-4}$-alkoxy.

12. A compound according to claim 10 wherein R¹ is hydrogen and R² is 4-methoxy-benzyl.

13. A process for the preparation of a malonamide derivative of formula IV,

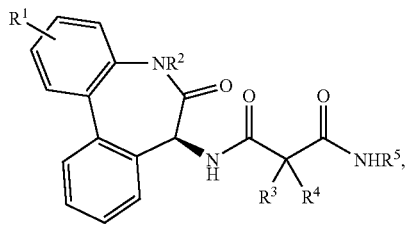

IV wherein:
- R¹ is hydrogen or halogen;
- R² is either $C_{1-4}$-alkyl optionally substituted with cycloalkyl or benzyl which is optionally substituted with $C_{1-4}$-alkoxy;
- R³ and R⁴ are each independently selected from the group consisting of: hydrogen, lower alkyl, lower alkoxy, phenyl and halogen;
- R⁵ is selected from the group consisting of: lower alkyl, lower alkynyl, —$(CH_2)_n$—O-lower alkyl, —$(CH_2)_n$—S-lower alkyl, —$(CH_2)_n$—CN, —$(CR'R'')_n$—$CF_3$, —$(CR'R'')_n$—$CHF_2$, —$(CR'R'')_n$—$CH_2F$, —$(CH_2)_n$—C(O)O-lower alkyl, —$(CH_2)_n$-halogen, and —$(CH_2)_n$-cycloalkyl, wherein said R⁵ is optionally substituted by one or more substituents selected from the group consisting of phenyl, halogen and —$CF_3$;
- R' and R'' are each independently selected from the group consisting of: hydrogen, lower alkyl, lower alkoxy, halogen and hydroxy; and
- n is 0, 1, 2, 3, or 4.;

said process comprising the preparation of an enantiomerically pure (S)-7-amino-5H,7H-dibenzo[b,d]azepin-6-one of formula I,

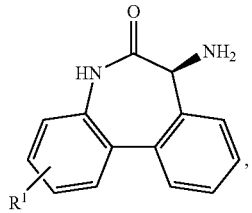

I wherein R¹ is as in the compound of formula IV, comprising the optical resolution of a dibenzo[b,d]azepinone derivative of the formula II,

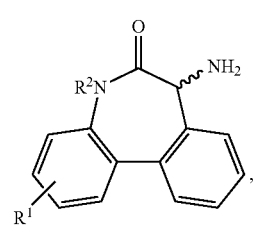

II wherein R¹ is as in the compound of formula I and R² is either $C_{1-4}$-alkyl optionally substituted with cycloalkyl or benzyl which is optionally substituted with $C_{1-4}$-alkoxy, using (−)-menthyl chloroformate.

* * * * *